US008896666B2

(12) United States Patent
Umemura

(10) Patent No.: US 8,896,666 B2
(45) Date of Patent: Nov. 25, 2014

(54) THREE-DIMENSIONAL MEASURING DEVICE AND BOARD INSPECTION DEVICE

(75) Inventor: Nobuyuki Umemura, Aichi (JP)

(73) Assignee: CKD Corporation, Aichi (JP)

( * ) Notice: Subject to any disclaimer, the term of this patent is extended or adjusted under 35 U.S.C. 154(b) by 837 days.

(21) Appl. No.: 12/944,525

(22) Filed: Nov. 11, 2010

(65) Prior Publication Data

US 2011/0249096 A1  Oct. 13, 2011

(30) Foreign Application Priority Data

Apr. 13, 2010 (JP) ................................. 2010-092403

(51) Int. Cl.
| | |
|---|---|
| H04N 13/02 | (2006.01) |
| G01B 11/06 | (2006.01) |
| H05K 3/34 | (2006.01) |
| G01N 21/956 | (2006.01) |
| G01B 11/25 | (2006.01) |
| G06K 9/00 | (2006.01) |

(52) U.S. Cl.
CPC ...... *G01B 11/0608* (2013.01); *H05K 2203/163* (2013.01); *H05K 3/3484* (2013.01); *G01N 21/956* (2013.01); *G01B 11/25* (2013.01)
USPC ........................................... 348/46; 382/150

(58) Field of Classification Search
USPC .......................................................... 348/46
See application file for complete search history.

(56) References Cited

U.S. PATENT DOCUMENTS

| | | | | |
|---|---|---|---|---|
| 2001/0002695 | A1* | 6/2001 | Takata et al. .................. | 250/226 |
| 2003/0129814 | A1* | 7/2003 | Mizukoshi .................... | 438/584 |
| 2007/0291189 | A1* | 12/2007 | Harville ............................ | 349/7 |
| 2009/0202143 | A1* | 8/2009 | Mamiya ........................ | 382/150 |
| 2010/0103194 | A1* | 4/2010 | Chen et al. .................... | 345/629 |

FOREIGN PATENT DOCUMENTS

| | | |
|---|---|---|
| JP | 07-050786 A | 2/1995 |
| JP | 2006-300539 A | 11/2006 |

* cited by examiner

*Primary Examiner* — Tung Vo
*Assistant Examiner* — Obafemi Sosanya
(74) *Attorney, Agent, or Firm* — Osha Liang LLP

(57) ABSTRACT

A board inspection device includes an irradiation device for irradiating light on a printed circuit board, a CCD camera for imaging the irradiated part of the circuit board. First image processing is performed for a first exposure time such that an inspection target region is free of brightness saturation, and second image processing is performed using a second exposure time corresponding to the insufficiency of the first exposure time relative to a certain exposure time appropriate for measurement of a measurement standard region. Thereafter, image data for three-dimensional measurement is prepared for the inspection target region using the value of image data obtained by the first image processing, and image data for three-dimensional measurement is prepared for the measurement standard region using a value obtained by summing the image data value acquired by the second image processing and the image data value acquired by the first image processing.

12 Claims, 4 Drawing Sheets

8,896,666 B2

THREE-DIMENSIONAL MEASURING DEVICE AND BOARD INSPECTION DEVICE

CROSS-REFERENCE TO RELATED APPLICATIONS

This Application claims priority to Japanese Patent Application No. 2010-92403 filed on Apr. 13, 2010 in Japan.

BACKGROUND OF INVENTION

1. Field of the Invention

The present invention generally relates to a three-dimensional measuring device and a board inspection device equipped with this three-dimensional measuring device.

2. Background Art

Generally, a printed circuit board is provided with an electrode pattern on a base substrate formed from glass-filled epoxy resin, and the printed circuit board is protected by a surface resist film. When an electronic component is mounted on this printed circuit board, cream solder is first printed on positions lacking protection by the resist film on the electrode pattern. Thereafter, the electronic component is temporarily fixed on the printed circuit board by use of the viscosity of this cream solder. Thereafter, this printed circuit board is placed in a reflow furnace, and the printed circuit board is subjected to a certain reflow step in order to perform soldering. There recently has been a need for inspection of the printed state of the cream solder prior to the printed circuit board being carried to the reflow furnace, and a three-dimensional measuring device is sometimes used during such inspection.

Various proposals have been made in recent years for three-dimensional measuring devices which use light, e.g., so-called non-contacting type three-dimensional measuring devices. For example, a three-dimensional measuring device using the phase shift method illuminates the object (e.g., printed circuit board) using a visible light source having a light pattern having a stripped light intensity distribution. Then, the object is imaged by a CCD camera. The phase differentials of the fringes of this light pattern are analyzed using the obtained image, and the three-dimensional shape, especially height, of the cream solder is measured.

However, various colors (e.g., background regions) are present within the range of the printed part of the cream solder on the printed circuit board. Such colors are due to the use of various colors for the glass epoxy resin and the resin film. This results in low contrast in the image data based on imaging by the CCD camera at a background region having a comparatively dark color (e.g., black). That is, the contrast of this light pattern (brightness difference) becomes small. Therefore, measurement of the brightness of the background region may become difficult. Standardization of heights within the board has previously been desirable for highly accurate measurement of the height of cream solder printed on the board. However, due to the inability to appropriately use the background region as a surface of standard height, it may be difficult to standardize height within the board.

Thus, technology has been proposed (see e.g., Japanese Patent Application Publication No. 2006-300539: JP2006-300539) for appropriate measurement of the height standard by performing separate imaging, for example, at an exposure time (e.g., 10 milliseconds (ms)) appropriate for the solder printing region (bright part) and at a different exposure time (e.g., 50 ms) for the background region (dark part).

Technology has also been proposed (see e.g., Japanese Patent Application Publication No. H7-50786: JPH7-50786) for increasing dynamic range by taking multiple images at exposure times (e.g., 10 ms each) such that the brightness of a pixel within the area corresponding to the bright part of the object is not saturated and by then summing the obtained multiple imaging data.

However, when imaging is performed separately for the solder printing region (bright part) and for the background region (dark part) as in JP2006-300539, a comparatively long time is required for obtaining all the required image data for performing three-dimensional measurement of a certain measurement object area (image area).

In a situation that the optimum exposure time for measurement of the solder printing region is 10 ms, the optimum exposure time for measurement of the height standard is 50 ms, and the time required for data transmission of each image data is 16 ms, the configuration of Patent Application Publication No. 2006-300539 requires a total time equal to 10 ms imaging time for the solder printing region+16 ms data transmission time+50 ms imaging time for the background region+16 ms data transmission time=92 ms.

Also, a great increase in the number of imaging operations occurs, as per JPH7-50786, by multiple imaging operations using exposure times such that brightness saturation does not occur for pixels within an area corresponding to the bright part of the measurement object. Thus, under assumed conditions similar to those described previously, a further prolonged time is required, e.g., total of 5 images (each having a 10 ms imaging time+a 16 ms data transmission time)=130 ms.

The time required for measurement of a single printed circuit board is further increased several fold when multiple measurement object areas (imaging areas) are established on the single printed circuit board or when 3 or 4 imaging operations are required for a single three-dimensional measurement using the phase shift method or the like.

SUMMARY OF INVENTION

One or more embodiments of the object of the present invention is to provide a three-dimensional measuring device, and a board inspection device, capable of realizing measurements of increasingly high accuracy during performance of three-dimensional measurement. Various embodiments of the present invention are described separately below.

In a first embodiment of the present invention, a three-dimensional measuring device includes an irradiation means capable of irradiating light for three-dimensional measurement onto a measurement object having a first area formed by objects under inspection and a second area forming a standard for measurement of height of the first area, an imaging means capable of imaging light reflected from the measurement object irradiated by the light, and an image processing means for three-dimensional measurement of the measurement object based on image data imaged by the imaging means; wherein the three-dimensional measuring device: performs first image processing by imaging for a first exposure time (e.g., 10 ms) such that brightness of a location corresponding to a bright part as either the first area or the second area is not saturated; performs second image processing by imaging for a second exposure time (e.g., 40 ms) corresponding to a time insufficiency, the insufficiency being between the first exposure time (e.g., 10 ms) and a certain exposure time (e.g., 50 ms) appropriate for measurement of a dark part of the first area or the second area; performs image preparation processing by combining a location of brightness non-saturation of imaging data obtained by the first image processing and a location of brightness non-saturation of imaging data obtained by the second image processing to prepare image data for three-dimensional measurement having no brightness saturation in the first area and the second area; and performs three-dimensional measurement based on the image data for three-dimensional measurement.

When imaging is performed with the goal of measurement of the first area, as described previously, sometimes for the second area in the image data the brightness value becomes excessively high, the brightness value becomes excessively low, or the difference between brightness values (brightness differential) becomes small. For example, when the second area is darkly colored in comparison to the first area, the brightness differential in the image data becomes comparatively small. On the other hand, when the second area is brightly colored in comparison to the first area, the brightness value of the second area in the image data may be saturated. Thus performance of three-dimensional measurement with good accuracy may be impossible using the second area as the height reference surface.

According to the first embodiment, image preparation is performed by combining the location of brightness non-saturation of imaging data obtained by combining the location of brightness non-saturation of image data imaged using the first exposure time free of brightness saturation at a location corresponding to the bright part and the location of brightness non-saturation of image data obtained at the second exposure time corresponding to the above-described insufficiency of the first exposure time (e.g., difference between the certain exposure time suitable for measurement of the dark part and the first exposure time). Thus, three-dimensional measurement in the dark part can be performed appropriately based on data of an extended dynamic range, and three-dimensional measurement in the bright part can be performed appropriately based on data free of brightness saturation. Thus, three-dimensional measurement can be performed appropriately in the second area, and therefore three-dimensional measurement of the first area can be performed with good accuracy using this second area as a height reference surface.

Also, according to the first embodiment, the time required for acquisition of all image data required for three-dimensional measurement of a certain measurement object area can be shortened.

For example, in a situation that the exposure time for non-saturation at a location corresponding to the bright area (e.g., no. 1 area) is 10 ms, the certain exposure time appropriate for measurement of the dark area (e.g., no. 2 area) is 50 ms, and the time required for data transmission of each image data is 16 ms, the time required for the first embodiment becomes a total of the imaging time (10 ms) for first image processing corresponding to the first exposure time+the data transmission time (16 ms)+the imaging time (40 ms) for second image processing corresponding to the second exposure time+the data transmission time (16 ms)=82 ms. That is, in comparison to the configuration of JP2006-300539, which describes performance of separate imaging operations with the object of measurement of the first area and measure of the second area, respectively, the first embodiment is able to reduce the time corresponding to the first exposure time by 10 ms (about 11%). Similarly, the first embodiment reduces the time by 48 ms (about 37%) in comparison to the configuration of JPH7-50786.

Thus, according to the above embodiment, measurement of increased accuracy can be achieved using a shorter time interval.

In a second embodiment of the present invention, during the image preparation processing for preparation of the image data for three-dimensional measurement, the value of data obtained by the first image processing is used for the location corresponding to the bright part, and a summed value obtained by adding of the value of the image data obtained by the first image processing and the value of the image data obtained by the second image processing is used for the location corresponding to the dark part.

According to the second embodiment, during production of the image data used for three-dimensional measurement, for both the first area and the second area (e.g., bright part and second part, respectively), the value of the image data obtained by the second image processing and the value of the image data obtained by the first image processing are summed together so that the adopted summed value is free of brightness saturation at the location corresponding to the bright part. However, at the location corresponding to the dark part, a value is obtained similar to that of the image data imaged at the certain exposure time (first exposure time+second exposure time) appropriate for measurement of the dark part.

Thus, during three-dimensional measurement processing, three-dimensional measurement (bright part measurement processing) is performed based on the value of image data obtained by the first image processing for the bright part, and three-dimensional measurement (dark part measurement processing) of the dark part is performed based on the value obtained by adding the value of image data obtained by the second image processing and the value of image data obtained by the first image processing.

Thus, the operational effect of the first embodiment can be achieved by use of relatively simple processing.

In a third embodiment of the present invention, the three-dimensional measuring device according to the second embodiment further includes a memory means for memory of a design data relating to the measurement object, and based on the design data, either the value of image data obtained by the first image processing or the summed value is selected for use during the image data preparation.

According to the third embodiment, during preparation of the image data used for three-dimensional measurement, based on previously stored design data, selection is made of either the first area or the second area, respectively, to use the value of image data obtained by the first image processing means or the above-described summed value, respectively. By this means, the processing procedure can be simplified and the speed of processing can be improved in comparison, for example, to a configuration that selects which data to use based on various types of information extracted from the image data imaged by the imaging means. These embodiments have the effect of further shortening the measurement time.

Also, according to the third embodiment, for example, if the color of the second area is dark in comparison to the first area, then the image data obtained by the first image processing is used for the first area, and the summed value is used for the second area.

In a fourth embodiment of the present invention, the above-described preparation of the image data for three-dimensional measurement using the above-described image preparation processing of the three-dimensional measuring device described in the first embodiment includes for each pixel the steps of: determining for the pixel whether or not brightness saturation occurs for a value obtained by summing the brightness value of image data of the pixel obtained by the first image processing and the brightness value of the pixel of image data obtained by the second image processing, using for the pixel the brightness value of the image data obtained by the first image processing if the determination was made that brightness saturation occurs, and using for the pixel the summed value if the determination was made that brightness saturation did not occur.

The fourth embodiment achieves an operational effect similar to that of the above-described second embodiment. In addition, this forth embodiment is able to adopt the above-described summed value as a brightness non-saturated value not only for the dark area but also for a location corresponding to the bright area. Since noise of the image element of a CCD or the like depends on the square root of the amount of received light, the differential between the signal and noise increases as the amount of received light increases, and obtaining image data of increasingly high accuracy is possible. This has the result of making possible the performance of measurement of higher accuracy.

In a fifth embodiment of the present invention, three-dimensional measurement of the three-dimensional measuring device according to any one of the above embodiments is performed by the phase shift method based on a multiplicity of the image data for three-dimensional measurement, each image data for three-dimensional measurement being obtained using a respective irradiation of light, and each irradiation having a respective phase differing from the phase of other irradiations.

Under the configuration of the fifth embodiment, the above-described operational effect of the first embodiment or the like is further achieved. Using three-dimensional measurement by the phase shift method, the phase of the irradiating light is changed over multiple phases, and multiple image data must be obtained, each phase having a different intensity distribution according each height level. That is, imaging must be performed each time the phase is changed, and multiple images must be taken for a certain measurement object area (image area). Thus, as the time required for a single imaging operation increases, the time required for obtaining all the image data required for performing three-dimensional measurement of this area increases several fold. Therefore, even if the time required for a single imaging operation is changed just slightly, this results in a large change in the required overall time.

In a sixth embodiment of the present invention, for the three-dimensional measuring device according to any one of the first through fifth aspects, the measurement object is a printed circuit board having an electrode pattern formed on a base substrate, the first area is a solder printing region where solder is printed on the electrode pattern, and the second area is the base substrate, a resist film covering the electrode pattern, or a region of the resist film covering the base substrate.

The term "solder printing region where solder is printed" here is taken to include the so-called solder region including the cream solder, silver paste region, conductive adhesive region, bump region, or the like.

A seventh embodiment of the present invention is a board inspection device equipped with the three-dimensional measuring device according to any one of the above embodiments.

According to the seventh embodiment, due to the board inspection device being equipped with the three-dimensional measuring device mentioned in any one of the above embodiments, efficient inspection of non-conforming products can be performed during the printed circuit board manufacturing process.

Other aspects and advantages of the invention will be apparent from the following description and the appended claims.

DETAILED DESCRIPTION

Embodiments of the present invention are explained below, referring to the attached figures. In embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid obscuring the invention.

Figure 1:
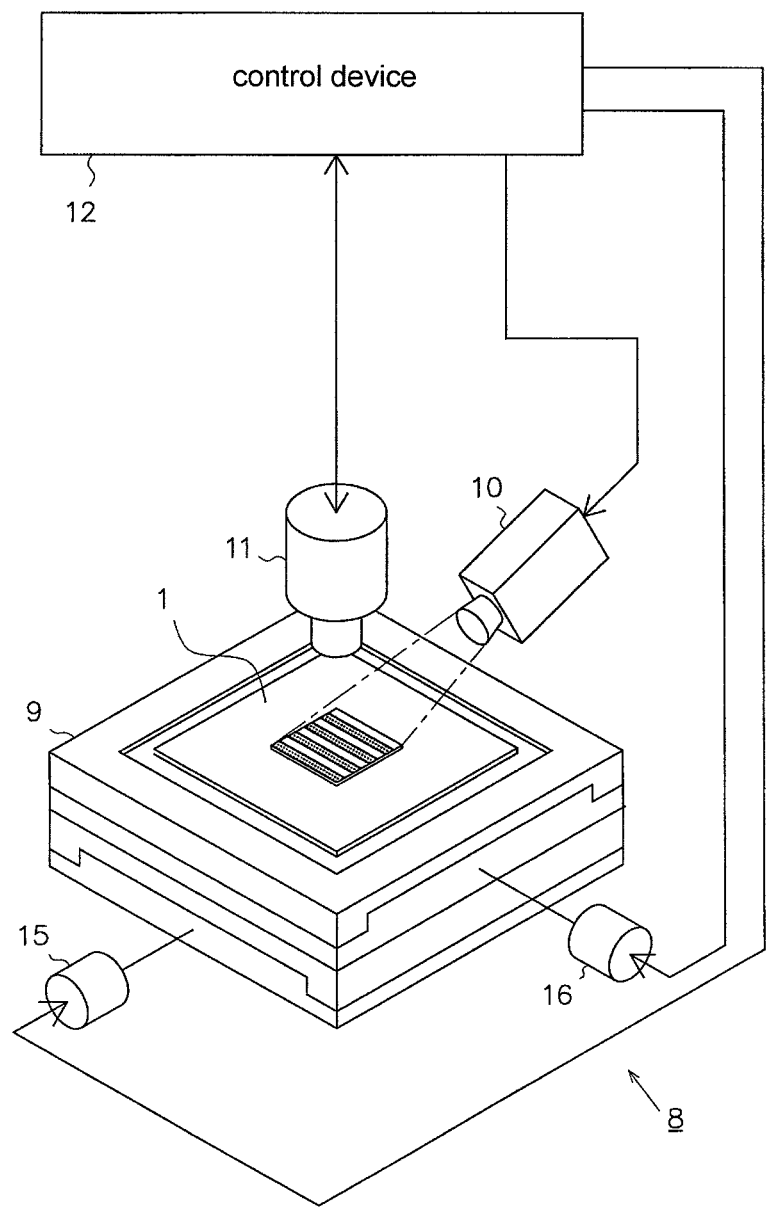
FIG. 1 shows a simplified tilted perspective view showing schematically the board inspection device according to one or more embodiments of the present invention.

FIG. 1 is a simplified structural drawing schematically showing the board inspection device equipped with the three-dimensional measuring device of this first embodiment. As shown in this figure, a board inspection device 8 includes a carrying stage 9 for carrying a printed circuit board 1, an irradiation device 10 as an irradiation means for irradiating a certain light component pattern onto the printed circuit board 1 surface from a tilted direction, a CCD camera 11 as an imaging means for imaging of the above-described irradiated part of the printed circuit board 1, and a control device 12 as a control means for execution of various types of control, image processing and calculation processing within the board inspection device 8.

The above-described carrying stage 9 is equipped with motors 15 and 16. These motors are driven and controlled by the control device 12 so that the printed circuit board 1 carried on the carrying stage 9 can be slid in any x-axis and y-axis direction.

Figure 2:
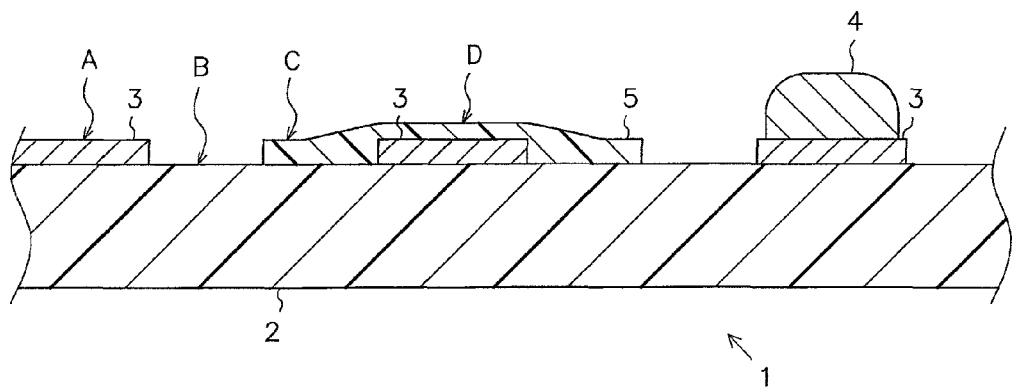
FIG. 2 shows a cross-sectional view of the printed circuit board according to one or more embodiments of the present invention.

As shown in FIG. 2, a printed circuit board 1 has a flat plate shape provided with a flat face. An electrode pattern 3 formed from copper foil is provided on a base substrate 2 formed from glass-epoxy resin or the like. A cream solder 4 is also printed onto a certain electrode pattern 4. This region where the cream solder 4 is printed it taken to be the "solder printing region." Although the parts outside of the solder printing regions are referred to collectively as the "background region," these parts include a region (A) where the electrode pattern 3 is exposed, a region (B) where the base substrate 2 is exposed, a region (C) where the a resist film 5 is coated on the base substrate 2, and a region (D) where the resist film 5 is coated on the electrode pattern 3. The resist film 5 is coated on the surface of the printed circuit board 1 so that cream solder 4 is not applied except at certain parts of the wiring. In the first embodiment, the background region is black or a grey color relatively close to black.

Figure 3:
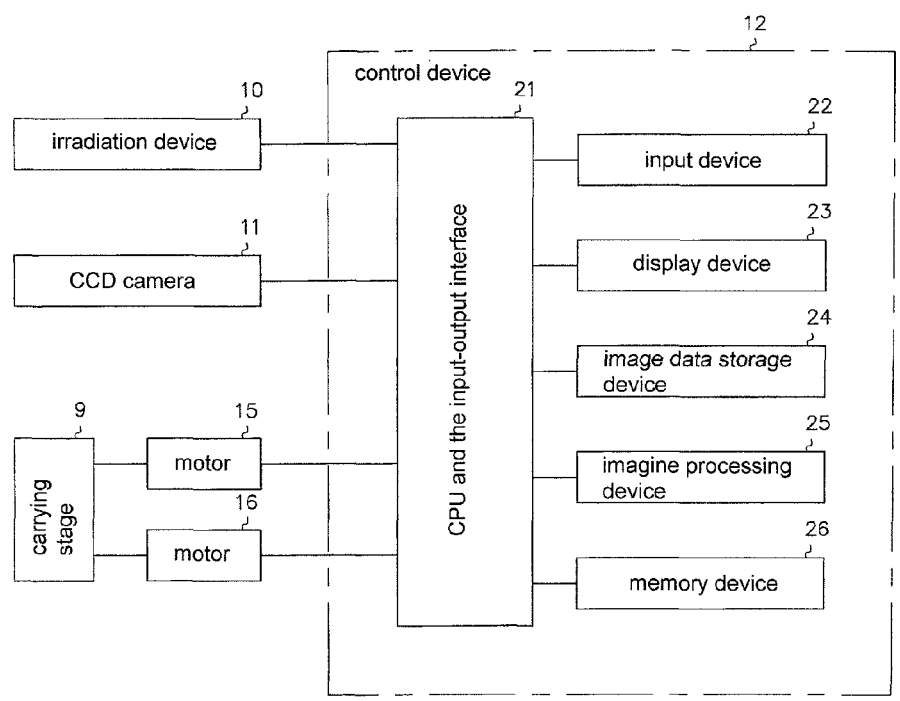
FIG. 3 shows a block diagram showing the gist of the board inspection device according to one or more embodiments of the present invention.

Electrical configuration of the control device 12 will next be explained. As shown in FIG. 3, the control device 12 is equipped with a CPU and an input-output interface 21 for performing overall control of the board inspection device 8, an input device 22 (e.g., keyboard, mouse, or touch panel), a display device 23 having a display screen (e.g., CRT, liquid crystal display, or the like), an image data storage device 24 for memory of image data or the like obtained by imaging by the CCD camera 11, an imagine processing device 25 as an image processing means for measurement of height or volume of the cream solder using the image from the CCD camera 11, and a memory device 26 as a memory means for memory of inspection results or design data, such as Gerber data. These devices 22 through 27 are electrically connected to the CPU and the input-output interface 21 (referred to hereinafter as the CPU 21 or the like).

Figure 4:
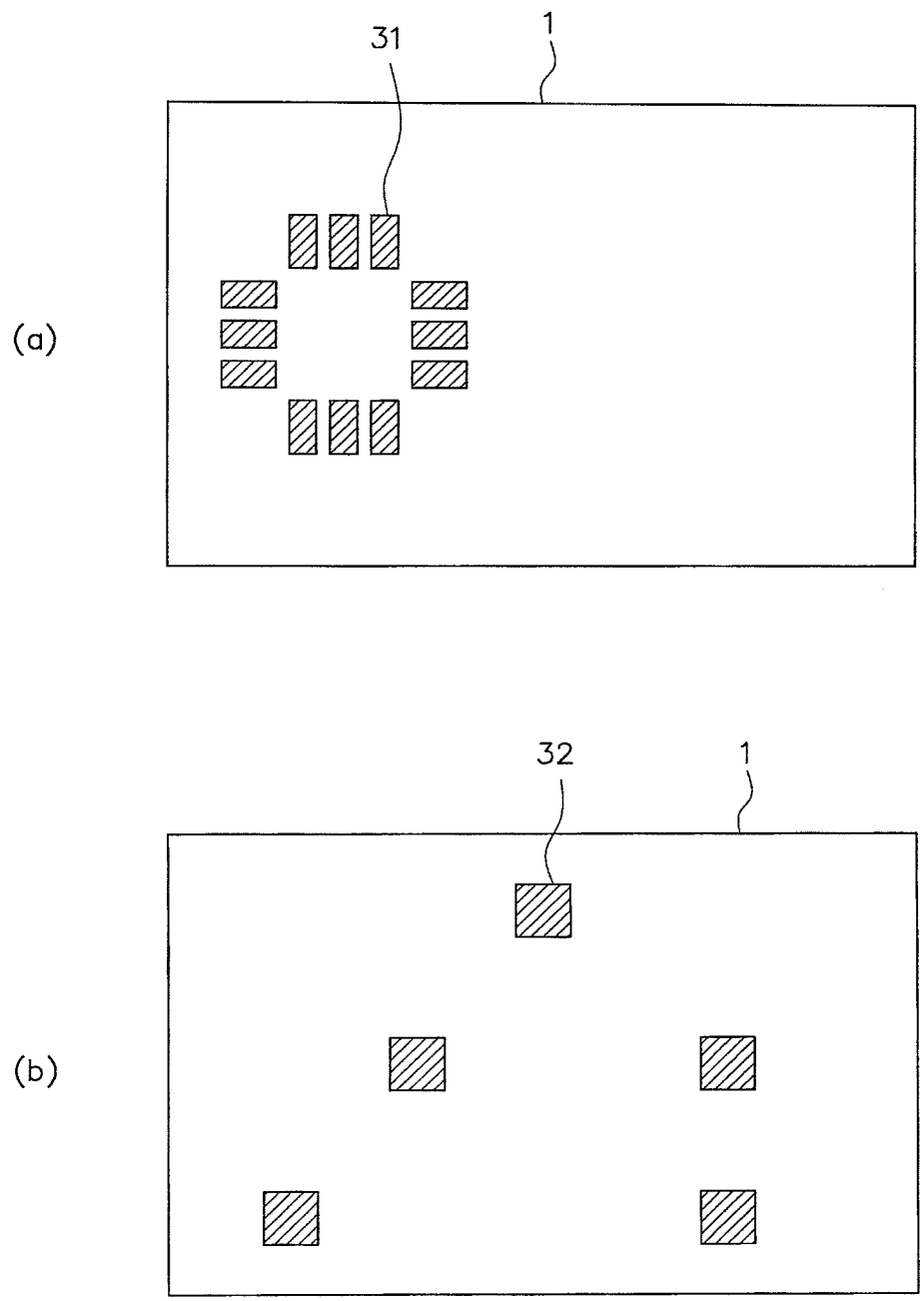
FIG. 4 shows an explanatory drawing for explanation of the inspection target region and the measurement standard region according to one or more embodiments of the present invention.

The inspection region or the like on the printed circuit board 1 will next be explained. Based on design data such as Gerber data, the inspection region or the like is established for the printed circuit board 1 (e.g., measurement object). For example as shown in FIG. 4 (*a*), an inspection target region 31 (region indicated by the hatched lines) as the "first area" forming an inspection object is established with respect to a solder printing region printed using cream solder 4. As shown in FIG. 4 (*b*), a measurement standard region 32 as the "second area" forming a standard for measurement of height is established relative to the background region.

An inspection field (measurement object area) is set beforehand on the printed circuit board 1. The printed circuit board 1 carried on the carrying stage 9 is slid in any x-axis and y-axis direction to fit this inspection field. Imaging by light pattern irradiation and CCD camera 11 imaging are performed for each of these inspection fields, and the printing condition of the cream solder 4 of the inspection target region 31 is inspected. The measurement standard region 32 is used as the height standard surface during this process.

Figure 5:
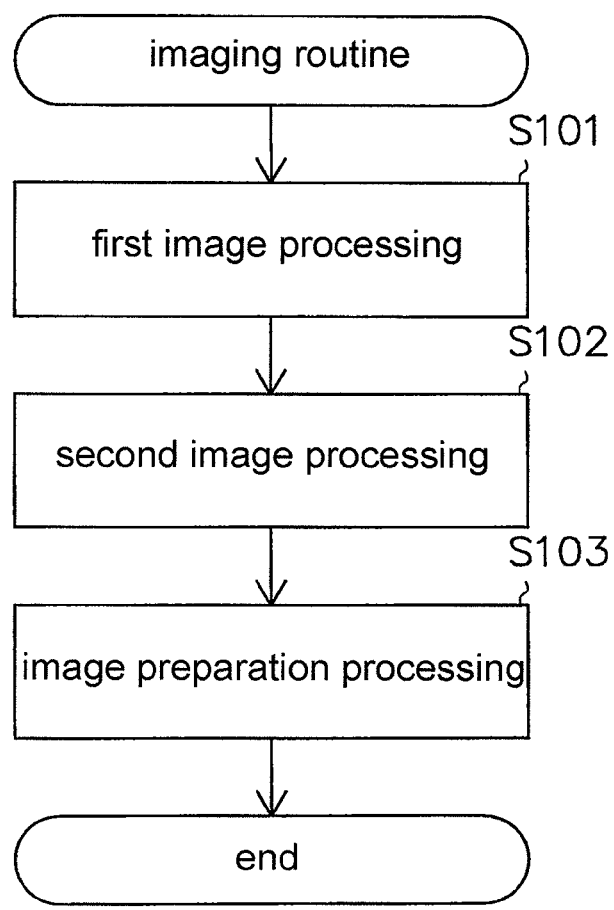
FIG. 5 shows a flow chart showing the imaging routine according to one or more embodiments of the present invention.

FIG. 5 will be used next to explain the imaging routine that is performed for each inspection field. This imaging routine is executed by the CPU 21 or the like During step S101 first image processing, the irradiation device 10 is turned ON, and a certain light component pattern is projected on the surface of the printed circuit board 1 from above at a tilted angle. Thereafter, due to a control signal from the CPU 21 or the like, the CCD camera 11 images the irradiated part. The image data acquired by the CCD camera 11 is transferred to the image data storage device 24 and is stored.

The imaging of the first image processing is performed for a first exposure time (10 ms in this first embodiment) that produces no brightness saturation at a location in the image data corresponding to the inspection target region 31 forming a bright part.

Thereafter, during the step S102 second image processing in a manner similar to the step S101 first image processing, the irradiation device 10 is turned ON, and a certain light component pattern is projected on the surface of the printed circuit board 1 from above at a tilted angle. Thereafter, due to a control signal from the CPU 21 or the like, the CCD camera 11 images the irradiated part. The image data acquired by the CCD camera 11 is transferred to the image data storage device 24 and is stored.

The second image processing step S102 differs from the first image processing step S101 in that imaging during the second image processing is performed using a second exposure time (40 ms in this first embodiment) corresponding to the insufficiency of the above-described first exposure time (10 ms) relative to a certain exposure time (50 ms in this first embodiment) suitable for measurement of the measurement standard region 32 forming the dark part.

During the step S103 image preparation processing, the image data acquired by the step S101 first image processing and the image data acquired by the step S102 second image processing are combined to produce image data for three-dimensional measurement such that the produced image data has no brightness saturation at the inspection target region 31 and the measurement standard region 32.

More specifically, image data acquired during the step S101 first image processing is used for locations corresponding to the inspection target region 31 (e.g., bright part) based on design data such as Gerber data. For locations corresponding to the measurement standard region 32 (e.g., dark part), the value of image data acquired during the step S101 first image processing is added to the value of image data acquired during the step S102 second image processing to prepare image data for three-dimensional measurement.

Under the below described assumptions (1) and (2), simple addition of the brightness values from the two imaging operations does not lower reliability of the brightness value.

(1) Noise generated by imaging is mostly photon shot noise (fluctuations in measurement values versus the true light intensity), and other noise (e.g., dark current, read-write noise, or the like) can be ignored. The standard deviation of the photon shot noise is equal to the square root of the number of photons.

(2) Photon shot noise is taken to be independent of the number of images. For example, when two images are simply added together, the resultant photon shot noise is taken to be equivalent to the square root (standard deviation) of the sum of the number of photons of the first image plus the number of photons of the second image.

Then, the image data for three-dimensional measurement prepared in this manner is stored by the image data storage device 24. At this point, the image routine relating to this inspection field is completed.

Thereafter, based on a multiplicity of the above-described image data for three-dimensional measurement obtained by the above-described routine by irradiation of a multiplicity of light component patterns (four irradiations in this first embodiment) having different phases, the image processing device 25 performs three-dimensional measurement processing (e.g., height measurement) of the inspection target region 31 and the measurement standard region 32 using the phase shift method. Thus, the height or volume of the cream solder 4 of the inspection target region 31 is measured while taking height of the measurement standard region 32 as the standard surface of height.

Based on this measurement value, the CPU 21 or the like inspects the printed state of the cream solder 4, makes a pass/fail determination, and stores the results of the inspection in the memory device 26. Moreover, a printed circuit board 1 determined to be non-conforming is ejected by a non-illustrated ejection mechanism.

According to the above-described embodiment, the imaging routine performed for each inspection field first image processing is performed using a first exposure time that does not cause brightness saturation at locations corresponding to the inspection target region 31 (solder printing region) forming the bright part, and second image processing is performed using a second exposure time corresponding to the insufficiency of the above-described first exposure time relative to a certain exposure time appropriate for measurement of the measurement standard region 32 (background region) forming the dark part.

Thereafter, for locations corresponding to the inspection target region 31 (e.g., bright part), image data for three-dimensional measurement is prepared by use of the image data acquired by the first image processing. For locations corresponding to the measurement standard region 32 (e.g., dark part), image data for three-dimensional measurement is prepared by summing of the image data acquired by the first image processing and the image data acquired by the second image processing.

Then, based on the multiplicity of three-dimensional measurement data obtained in this manner, for the inspection target region 31, three-dimensional measurement is performed based on the value of the image data free of brightness saturation obtained by the first image processing. For the measurement standard region 32, three-dimensional measurement is performed based on similar values of image data imaged at a certain time (e.g., the first exposure time plus the second exposure time) appropriate for measurement of the measurement standard region 32. That is, three-dimensional measurement can be performed appropriately for the measurement standard region 32 based on data having an expanded dynamic range, and three-dimensional measurement can be performed appropriately for the inspection target region 31 based on data free of brightness saturation.

As a result, three-dimensional measurement can be performed appropriately for the measurement standard region 32, and thus three-dimensional measurement can be performed with good accuracy for cream solder 4 while using this measurement standard region 32 as the height standard surface.

According to the above-described embodiment, the time required for acquiring all the required image data in addition to performing three-dimensional measurement for each inspection field can be reduced.

For example, in a situation that the data transmission time required for transmission of each image data is 16 ms, the total time required according to this first embodiment is the equal to 4 times the sum of the image time (10 ms) of the first image processing corresponding to the first exposure time+ data transfer time (16 ms)+image time (40 ms) of the second image processing corresponding to the second exposure time+data transfer time (16 ms)=4 times 82 ms. That is, in comparison to the above-described configuration of Patent Citation 1, which performed one respective imaging each with the object of measurement of the inspection target region 31 and with the object of measurement of the measurement standard region 32, this first embodiment is able to reduce the total required time by a time (40 ms) corresponding to 4 times the above-described first exposure time (10 ms). In a similar manner, in comparison to the above-described configuration of Patent Citation 2, this first embodiment is able to reduce the total required time by a time (192 ms) corresponding to 4 times 48 ms.

Thus, according to the first embodiment, measurement of increased accuracy can be realized during a shorter time interval.

Also, during preparation of the image data for three-dimensional measurement, the first embodiment uses, based on previously stored design data, either the value of the image data acquired by the first image processing for the inspection target region 31 or the above-described summed value for the measurement standard region 32. By this means, simplification of the processing procedure and improvement of processing speed are possible in comparison, for example, to a configuration that determines which data to use based on various types of information extracted from the image data imaged by the CCD camera 11.

The present invention is not limited to the details of the above-described first embodiment. Of course, other applications and modifications are possible. Some other applications and modifications are illustrated by the below listed examples.

(a) The above-described first embodiment is an example of measurement of a printed circuit board 1 on which the measurement standard region 32 (background region) is darker than the inspection target region 31 (solder printing region), and where the printed circuit board 1 is black colored or is a gray color relatively close to black. In a second embodiment, measurement is possible of a printed circuit board 1 on which the measurement standard region 32 is brighter than the inspection target region 31, e.g., where the printed circuit board 1 background region is white colored or a gray color relatively close to white. In this second embodiment, brightness at the measurement standard region 32 becomes excessively high (greater than brightness of the inspection target region 31), resulting in brightness saturation. Thus, for example, image data for three-dimensional measurement is prepared for locations corresponding to the measurement standard region 32 (bright part) image data acquired by the first image processing, and image data for three-dimensional measurement is prepared for locations corresponding to the inspection target region 31 (dark part) using values obtained by summing the image data acquired by the second image processing and the image data acquired by the first image processing.

(b) Although the first embodiment describes measurement of height or the like of cream solder 4 printed on the printed circuit board 1, a third embodiment, is also applicable as an inspection device used for a wafer substrate, mounting board, or the like. For example, in the case of a wafer substrate, surface of the oxide layer can be used as the standard height, and calculation becomes possible of solder bump height, shape, volume, or the like.

(c) In the first embodiment, the phase shift method is adopted as the three-dimensional measurement method. However, a forth embodiment is possible that adopts another three-dimensional measurement method such as the Moiré method or the like.

(d) The first embodiment is configured to use, based on previously stored design data such as Gerber data or the like, either the value of the image data acquired by the first image processing for the inspection target region 31 for the locations corresponding to the inspection target region 31 (bright part) or the summed value of the image data acquired by the second image processing and the image data acquired by the first image processing for the measurement standard region 32 (dark part).

However, this configuration of the first embodiment is not limiting. A fifth embodiment is also possible for performing multiple imaging routines during performance of three-dimensional measurement according to the phase shift method as in the first embodiment, but where, if one brightness value is saturated among the various pixels of multiple image data imaged by the first image processing during multiple imaging operations, the value of image data acquired by the second image processing is used rather than the value of the image data acquired by the first image processing.

Alternatively for example, a sixth embodiment is possible in which, when brightness is determined to be saturated among the values obtained by summing the brightness value of each pixel of image data acquired by the first image processing and the brightness value of each pixel of image data acquired by the second image processing means, the brightness value of the image data acquired by the first image processing is used for such a pixel during preparation of image data for three-dimensional measurement, and the above-described summed value is used during preparation of image data for three-dimensional measurement for pixels free of brightness saturation.

In this manner, even for locations corresponding to bright parts and not just dark parts, use of the above-described summed value is possible when this summed value is free of brightness saturation. Due to dependence of the noise of the CCD, etc. imaging element on the square root of the amount of received light, the difference between the signal and noise increases as the amount of received light increases, and acquisition of image data of higher accuracy is possible. This makes performance of measurement possible with further increased accuracy.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A three-dimensional measuring device comprising:
   an irradiation means capable of irradiating light for three-dimensional measurement onto a measurement object having a first area formed by objects under inspection and a second area forming a standard for measurement of height of the first area,
   an imaging means capable of imaging light reflected from the measurement object irradiated by the light, and
   an image processing means for three-dimensional measurement of the measurement object based on image data imaged by the imaging means;
   wherein the three-dimensional measuring device:
   performs three-dimensional measurement based on the image data for three-dimensional measurement.
   performs first image processing by imaging for a first exposure time such that brightness of a location corresponding to a bright part as either the first area or the second area is not saturated;
   performs first data transmission of image data obtained by the first data image processing;
   performs second image processing by imaging for a second exposure time corresponding to a time insufficiency, the insufficiency being between the first exposure time and a certain exposure time appropriate for measurement of a dark part of the first area or the second area;
   performs second data transmission of image data obtained by the second image processing; and
   performs image preparation processing by combining a location of brightness non-saturation of imaging data obtained by the first image processing and a location of brightness non-saturation of imaging data obtained by the second image processing to prepare image data for three-dimensional measurement having no brightness saturation in the first area and the second area;
   performs three-dimensional measurement based on a surface image formed by the image data for three-dimensional measurement;
   wherein, during the image preparation processing for preparation of the image data for three-dimensional measurement, the value of data only obtained by the first image processing is used for the location corresponding to the bright part, and a summed value obtained by adding of the value of the image data obtained by the first image processing and the value of the image data obtained by the second image processing is used for the location: i corresponding to the dark part;
   wherein three-dimensional measurement is performed by the phase shift method based on a multiplicity of the image data for three-dimensional measurement, each image data for three-dimensional measurement being obtained using a respective irradiation of light, and each irradiation having a respective phase differing from the phase of other irradiations.

2. The three-dimensional measuring device according to claim 1,
   wherein the device further comprises a memory means for memory of a design data relating to the measurement object; and
   wherein based on the design data, either the value of image data obtained by the first image processing or the summed value is selected for use during the image preparation processing.

3. The three-dimensional measuring device according to claim 1,
   wherein the preparation of the image data for three-dimensional measurement during the image preparation processing comprises, for each pixel, the steps of:
   determining for the pixel whether or not brightness saturation occurs for a value obtained by summing the brightness value of image data of the pixel obtained by the first image processing and the brightness value of the pixel of image data obtained by the second image processing;
   using for the pixel the brightness value of the image data obtained by the first image processing if the determination was made that brightness saturation occurs; and
   using for the pixel the summed value if the determination was made that brightness saturation did not occur.

4. The three-dimensional measuring device according to claim 2,
   wherein three-dimensional measurement is performed by the phase shift method based on a multiplicity of the image data for three-dimensional measurement, each image data for three-dimensional measurement being obtained using a respective irradiation of light, and each irradiation having a respective phase differing from the phase of other irradiations.

5. The three-dimensional measuring device according to claim 3,
   wherein three-dimensional measurement is performed by the phase shift method based on a multiplicity of the image data for three-dimensional measurement, each image data for three-dimensional measurement being obtained using a respective irradiation of light, and each irradiation having a respective phase differing from the phase of other irradiations.

6. The three-dimensional measuring device according to claim 1,
   wherein the measurement object is a printed circuit board having an electrode pattern formed on a base substrate;
   wherein the first area is a solder printing region where solder is printed on the electrode pattern; and
   wherein the second area is an area selected from among a group consisting of:
   the base substrate, a resist film covering the electrode pattern, and a region of the resist film covering the base substrate.

7. A board inspection device comprising the three-dimensional measuring device according to claim 1.

8. A board inspection device comprising the three-dimensional measuring device according to claim 6.

9. The three-dimensional measuring device according to claim 2,
   wherein the measurement object is a printed circuit board having an electrode pattern formed on a base substrate;

wherein the first area is a solder printing region where solder is printed on the electrode pattern; and wherein the second area is an area selected from among a group consisting of:

the base substrate, a resist film covering the electrode pattern, and a region of the resist film covering the base substrate.

10. The three-dimensional measuring device according to claim 3, wherein the measurement object is a printed circuit board having an electrode pattern formed on a base substrate;

wherein the first area is a solder printing region where solder is printed on the electrode pattern; and wherein the second area is an area selected from among a group consisting of:

the base substrate, a resist film covering the electrode pattern, and a region of the resist film covering the base substrate.

11. A board inspection device comprising the three-dimensional measuring device according to claim 2.

12. A board inspection device comprising the three-dimensional measuring device according to claim 3.

* * * * *